United States Patent
Warner et al.

(10) Patent No.: US 9,259,156 B2
(45) Date of Patent: Feb. 16, 2016

(54) METHODS AND SYSTEMS TO TRANSLATE TWO DIMENSIONAL MAPPING INTO A THREE DIMENSIONAL DERIVED MODEL

(71) Applicant: General Electric Company, Schenectady, NY (US)

(72) Inventors: Adrian F. Warner, Wauwatosa, WI (US); Claudio Patricio Mejia, Wauwatosa, WI (US); Daniel Richard Schneidewend, Wauwatosa, WI (US); Maxime Cazalas, Buc (FR)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/328,089

(22) Filed: Jul. 10, 2014

(65) Prior Publication Data

US 2016/0007852 A1     Jan. 14, 2016

(51) Int. Cl.
| | |
|---|---|
| A61B 5/044 | (2006.01) |
| A61B 5/00 | (2006.01) |
| A61B 5/042 | (2006.01) |
| A61B 6/00 | (2006.01) |
| A61B 5/055 | (2006.01) |

(52) U.S. Cl.
CPC .............. *A61B 5/0035* (2013.01); *A61B 5/042* (2013.01); *A61B 5/044* (2013.01); *A61B 5/055* (2013.01); *A61B 5/6858* (2013.01); *A61B 5/7275* (2013.01); *A61B 6/485* (2013.01); *A61B 6/504* (2013.01); *A61B 6/5247* (2013.01)

(58) Field of Classification Search
None
See application file for complete search history.

(56) References Cited

U.S. PATENT DOCUMENTS

| | | | |
|---|---|---|---|
| 5,054,496 A * | 10/1991 | Wen et al. ...................... 600/509 |
| 5,687,737 A * | 11/1997 | Branham et al. ............... 600/523 |
| 5,798,761 A | 8/1998 | Isaacs |
| 6,603,996 B1 * | 8/2003 | Beatty et al. ................... 600/513 |
| 8,184,886 B2 | 5/2012 | Khamene et al. |
| 8,274,506 B1 | 9/2012 | Rees |
| 8,472,746 B2 | 6/2013 | Wei et al. |
| 2010/0097374 A1* | 4/2010 | Fan et al. ....................... 345/420 |
| 2014/0071130 A1 | 3/2014 | Piemonte |
| 2014/0107453 A1* | 4/2014 | Maskara et al. ............... 600/374 |
| 2014/0187989 A1* | 7/2014 | Thakur et al. ................. 600/509 |
| 2014/0200457 A1* | 7/2014 | Shuros et al. .................. 600/466 |
| 2014/0235988 A1* | 8/2014 | Ghosh ........................... 600/374 |
| 2015/0119671 A1* | 4/2015 | Varma ........................... 600/374 |

* cited by examiner

*Primary Examiner* — Kennedy Schaetzle
(74) *Attorney, Agent, or Firm* — Dean D. Small; The Small Patent Law Group, LLC.

(57) ABSTRACT

A method and system for translating two dimensional (2D) mapping into a three dimensional (3D) derived model. The method and system receive electrical measurements from a plurality of electrodes of the basket catheter of an anatomical region of interest. The method and system receive a 2D map grid based on the electrodes and corresponding spines of the basket catheter. The 2D map grid includes a location of at least one focus of an arrhythmic rotor. Further, the method and system generate a 3D derived model of the anatomical region of interest that includes the basket catheter and display a 3D location of the focus the arrhythmic rotor on the 3D derived model based on the 2D map grid.

20 Claims, 7 Drawing Sheets

METHODS AND SYSTEMS TO TRANSLATE TWO DIMENSIONAL MAPPING INTO A THREE DIMENSIONAL DERIVED MODEL

BACKGROUND OF THE INVENTION

The subject matter disclosed herein relates generally to systems and methods for translating a two dimensional (2D) mapping into a three dimensional (3D) derived model of an anatomic region of interest of a patient.

An arrhythmia or irregular heartbeat occurs when the electrical activity of the heart of a patient is irregular or is faster or slower than normal. The electrical activity of the heart may be measured by a catheter with electrodes positioned against the heart wall. Conventionally, these measurements may be used to create a 2D map of the electrical activity based on the positions of the electrodes relative to the catheter. Further, based on the 2D map and electrical measurements a rotor can be identified. A rotor is a foci of an arrhythmic event. Once the rotor is identified, a clinician can treat the arrhythmia by positioning a medical tool, such as an ablation catheter, at the rotor. However, there is a need to translate the position of the rotor from the 2D map based on the electrode position of the catheter to a 3D position based on the anatomy of the patient, such as the heart.

BRIEF DESCRIPTION OF THE INVENTION

Certain embodiments of the present disclosure provide, a method for translating two dimensional (2D) mapping into a three dimensional (3D) derived model of an anatomical region. The method may also include receiving electrical measurements from a plurality of electrodes of a basket catheter of an anatomical region of interest, and receiving a 2D map grid based on the electrodes and corresponding spines of the basket catheter. The 2D map grid includes a location of at least one focus of an arrhythmic rotor. The method further may include generating a 3D derived model of the anatomical region of interest, and displaying a 3D location of the focus of the arrhythmic rotor on the 3D derived model based on the 2D map.

Certain embodiments of the present disclosure provide, a system that may include a basket catheter and a two dimensional (2D) mapping subsystem communicatively coupled to the basket catheter and an image processing subsystem. The 2D mapping subsystem may be configured to generate a 2D map grid based on electrical measurement from a plurality of electrodes received from the basket catheter. The 2D map grid may include a location of at least one focus of an arrhythmic rotor. The image processing subsystem may be configured to display a 3D location of the focus of the arrhythmic rotor on the 3D derived model based on the 2D map grid.

DETAILED DESCRIPTION OF THE INVENTION

Figure 1:
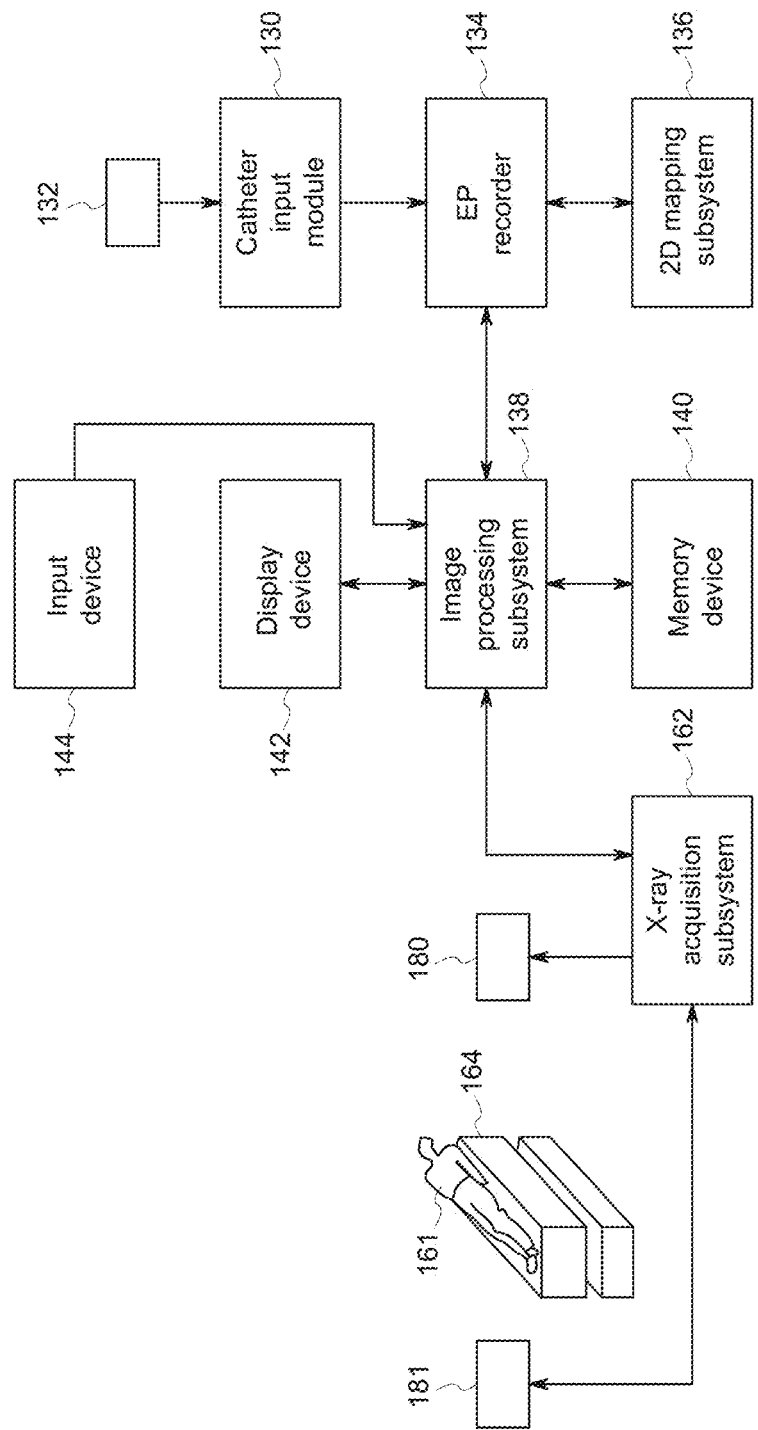
FIG. 1 is a schematic diagram illustrating a system for translating two dimensional mapping into a three dimensional derived model, according to an embodiment.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," "subsystems," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for translating two dimensional mapping to a three dimensional derived model. For example, various embodiments provide for a medical tool, such as a basket catheter, that acquire electrical information from an anatomical region of interest (e.g., a heart) from a patient. The selection of the medical tool may be based on a three dimensional model size acquired from the patient. The three dimensional model allows a physician to check a potential fit of the basket catheter to be moved over the heart chamber. Once the selected basket catheter is deployed into the chamber(s) of the heart, a two dimensional image may be acquired and registered with the three dimensional model to display a three dimensional derived model of the anatomy of the patient. Location markers relative to features of the basket catheter may be marked on the three dimensional derived model to provide a user reference for a clinician (e.g., medical doctor).

The basket catheter may be spread out in a way that the location of the electrodes may be used to form a two dimensional map. The two dimensional map is used to interpret electrical signal information such that a location of a rotor may be determined that represents the arrhythmic action within the substrate of the heart. From the two dimensional map, the system and method provides a reference of the rotor on the three dimensional derived model.

Once the position of the rotor is identified, the clinician may insert an ablation catheter and navigate the ablation catheter to the marked rotor on the three dimensional derived model. The rotor may then be burned using the ablation catheter to eliminate the source of the arrhythmia.

Various embodiments provide translation from a two dimensional rotor foci mapping to a three dimensional x-ray derived model to allow a clinician to easily translate for the clinician an improved estimate of the appropriate sized basket catheter to electrical location relative to the physical anatomy of the patient. At least one embodiment provides a clinician a better estimation of the appropriate sized basket catheter, thereby helping to minimize costly waste in the procedure though inappropriate sized catheter deployment. At least one embodiment provides faster and more accurate location of the loci from the two dimensional rotor foci mapping relative to the patient anatomy. At least one embodiment provides faster more accurate location of the target for the ablation burn.

FIG. 1 illustrates a system 120 for translating two dimensional mapping into a three dimensional derived model, accordance to an embodiment. In the illustrated embodiment, the system 120 includes an X-ray acquisition subsystem 162, a catheter input module 130, an electrophysiology (EP) recorder 134, a two dimensional (2D) mapping subsystem 136, an image processing subsystem 138, a memory device 140, a display device 142 (e.g., LCD screen, plasma screen, computer display), and an input device 144 (e.g., keyboard, computer mouse, touchscreen interface).

The X-ray acquisition subsystem 162 may be provided to generate a three dimensional (3D) model of an anatomical region of interest (e.g., heart) of a patient 166. The X-ray acquisition subsystem 162 may operate an X-ray source 180 and an X-ray detector 181. The X-ray acquisition system 162 may include a computed tomography (CT) imaging system, a magnetic resonance (MR) imaging system, a 3D rotation angiography, or the like. The X-ray source 180 generates X-rays that propagate through the anatomical region of a patient 166. The X-ray detector 181 detects the X-rays that have propagated through the patient 166 and generates data that is transferred to the X-ray acquisition subsystem 162. The X-ray acquisition subsystem 162 generates a 3D model of the anatomical region utilizing the data from the X-ray detector 181. The X-ray acquisition subsystem 162 may operably communicate with the image processing subsystem 138. Further, the X-ray acquisition subsystem 162 may transfer the 3D model of the anatomical region to the registration subsystem 138. Additionally or alternatively, the 3D model of the anatomical region of the patient 166 may be generated by an anatomical template or a priori information of the patient 166 stored on the memory 140 and/or the X-ray acquisition subsystem 162.

Additionally or alternatively, the X-ray acquisition subsystem 162 may generate a plurality of two dimensional (2D) images of the anatomical region of the patient 166. For example, the X-ray acquisition subsystem 162 may generate a 2D image of the anatomical region during a predetermine phase of a surgical procedure, such as a deployment of a basket catheter 132 into the anatomical region (e.g., the heart). Additionally or alternatively, the X-ray acquisition subsystem 162 may generate the 2D image of the anatomical region during a predetermine phase of the cardiac cycle based on measurements of a heart monitoring system (e.g., electrocardiogram). Optionally, the X-ray source 180 and the X-ray detector 181 may be disposed at opposite ends of a c-arm support structure (not shown), and disposed on opposite sides of the patient 116 as the patient lays on a table 164.

Optionally, the X-ray acquisition subsystem 162 may be communicatively coupled to additional X-ray sources 180 and/or X-ray detectors 181, such that the X-ray acquisition subsystem 162 may acquire a 3D model and 2D images of the anatomical region of the patient 166.

In at least one embodiment, the X-ray acquisition subsystem 162 may generate 2D images of the anatomical region in response to a control signal received from the image processing subsystem 138, input device 144, or the like indicating that the basket catheter 132 is deployed within the anatomical region. The X-ray acquisition subsystem 162 may transfer the 2D image of the anatomical region to the image processing subsystem 138.

The catheter input module 130 is communicatively coupled to the basket catheter 132 and the EP recorder 134. The catheter input module 130 is provided to modify, filter (as needed), and sample electrical signals received from the basket catheter 132 to the EP recorder 134. In at least one embodiment, the catheter input module 130 converts the electrical signals received from the basket catheter 132 to a digital domain.

The basket catheter 132 may be inserted through the venous system in the heart (e.g., the anatomical region of interest). Once the basket catheter 132 is in position, the basket catheter 132 may be expanded or deployed into the heart chamber, such that a plurality of electrodes 222-236 of the basket catheter 132 are in contact with the heart wall. Once deployed, the basket catheter 132 may monitor electrical activity of the heart. In particular, the electrodes 222-236 of the basket catheter 132 may detect and/or measure amplitudes, frequency, and the like of electrical signals within the heart corresponding to positions of the electrodes 222-236. The basket catheter 132 sends raw electrical measurements to the catheter input module 130 indicative of the amplitude of the electrical signals in the heart.

Figure 2:
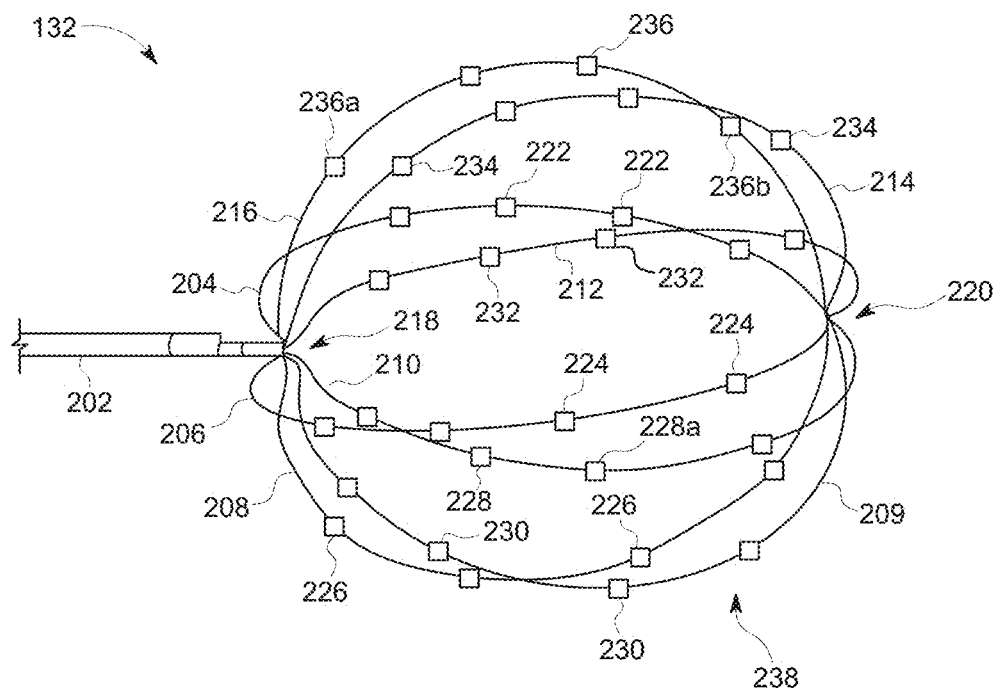
FIG. 2 is a perspective view of a basket catheter, in accordance with an embodiment.

FIG. 2 is a perspective view of the basket catheter 132, in accordance with an embodiment. In the illustrated embodiment, the basket catheter 132 includes an electrode assembly or basket 238 protruding from a distal end 218 of a sheath 202. The electrode assembly 238 is illustrated in an expanded state, forming a generally spherical shape. It should be noted that the electrode assembly 238 may transition freely between a collapsed state and the expanded state by varying a force applied to the basket catheter 200. The transition may be achieved by using a shape memory material or some other biasing mechanism. For example, the clinician through the input device 144 may instruct the a catheter control subsystem (not shown) to apply a force to the basket catheter 132, which may cause the basket catheter 132 to enter a collapsed state, and upon removal of the force may return the basket catheter 132 to the expanded state.

The electrode assembly 238 is illustrated having eight spines 204-216. Each of the spines 204-216 has a distal 220 and a proximal end 218. It should be noted, that in alternative embodiments the electrode assembly 238 may have a different number of spines, for example, fewer than or greater than the eight spines 204-216 shown in FIG. 2. The spines are deflectable elongated pieces that carry a plurality of electrodes 222-236 along a length of the spines 204-216. It should be noted, that in alternative embodiments the spines 204-216 may each have fewer or greater than the number of electrodes 222-236 shown in FIG. 2. When the electrode assembly 238 is in the expanded state, the electrodes 222-236 on the spines 204-216 form an array of electrodes distributed over a substantially spherical surface.

The EP recorder 134 receives the electrical measurements from the catheter input module 130 and outputs the electrical measurements to the 2D mapping system 136. In at least one embodiment, the image processing subsystem 138 receives the electrical measurements from the EP recorder 134. The electrical measurements may be received by the 2D mapping system 136 and image processing subsystem 138 in real time (e.g., during acquisition of the electrical measurements by the basket catheter 132), near real time, or non-real time while the basket catheter 132 is within the heart.

Figure 3:
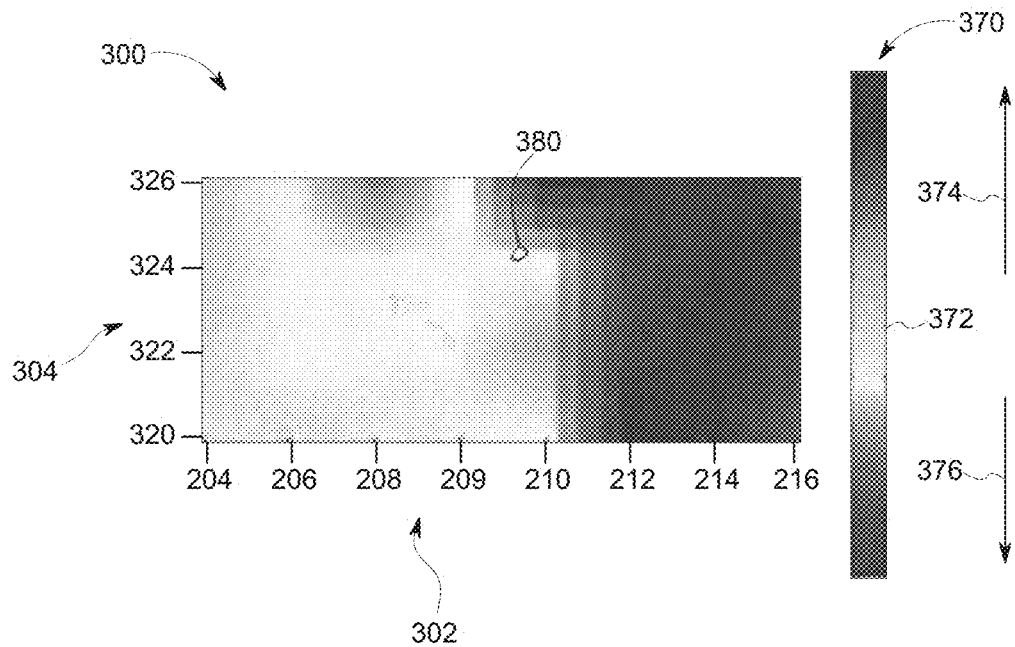
FIG. 3 is a two dimensional map grid of the electrical measurements of a basket catheter, in accordance with an embodiment.

The 2D mapping subsystem 136 may generate a 2D map grid (e.g., 2D matrix) 300 from the 3D space measured by the electrical measurements based on the position of the electrodes 222-236 of the basket catheter 132 in the heart. The 2D map grid 300 may be formed by translating the spines 204-216 and electrodes 222-236 on an axis 302 and 304, respectively. FIG. 3 illustrates the 2D map grid 300 based on the electrical measurements received by the 2D mapping subsystem 136 from the EP recorder 134. Optionally, the 2D map grid 300 may be displayed on the display device 142. The horizontal axis 302 is divided into spines 204-216 of the basket catheter 134. The vertical axis 304 represents an electrode group 320-326 of the spines 204-216 based on its position relative to the distal end 218 of the sheath 202. For example, the electrode group 320 may represent the electrodes proximate to the sheath 202 with respect to each spine 204-216 (e.g., the electrode 236a of the spine 216), and the electrode group 326 may represent the electrodes proximate to the distal end 220 of the electrode assembly 238 (e.g., the electrode 236b of the spine 216).

The 2D map grid 300 includes predetermined contrast levels that correspond to the electrical activation time based on the electrical measurements and cardiac cycle. A contrast bar 370 illustrates the predetermined contrast levels. For example, based on a cardiac cycle measured by a heart monitoring system (e.g., electrocardiogram), a normal electrical activation time is at 372. An electrical activation time moving in the direction of the arrow 374, pointing away from the normal electrical activation time at 372, corresponds to a later activation time, which may indicate an arrhythmic event. An electrical activation time in the direction of the arrow 376, pointing away from the normal electrical activation time at 372, corresponds to an earlier activation time, which may indicate an arrhythmic event. It should be noted, that in certain embodiments a predetermined color scheme may be used to indicate the electrical activation time.

Optionally, the 2D mapping subsystem 136 may determine a location of a rotor foci (focus of the arrhythmic event source) providing a region of interest (ROI) with respect to the two axes 302 and 304, which correlate to a position relative to the basket catheter 132. The 2D mapping subsystem 136 may send or transmit the ROI to the EP recorder 134, which may be accessed by the clinician and image processing subsystem 138. For example, the 2D mapping subsystem 136 may determine that a rotor foci 380 is located within the 2D map grid 300. Based on the location of the rotor foci 380, the 2D mapping subsystem 136 may determine that the rotor foci 380 is positioned proximate to the electrode 228a of the spine 210. The 2D mapping subsystem 136 may transmit the ROI to the EP recorder 134, which may be accessed by the image processing subsystem 138. Optionally, the display device 142 may indicate the ROI and/or rotor foci 380 on the 2D map grid. Additionally or alternatively, the 2D mapping subsystem 136 may receive from the input device 144 a location of the rotor foci 380 once the 2D map grid 300 is displayed on the display device 142. In at least one embodiment, the basket catheter 132 may be monitored by a position monitoring circuit using conventional techniques, which is received by the image processing subsystem 138 from the EP recorder 134.

Figure 4:
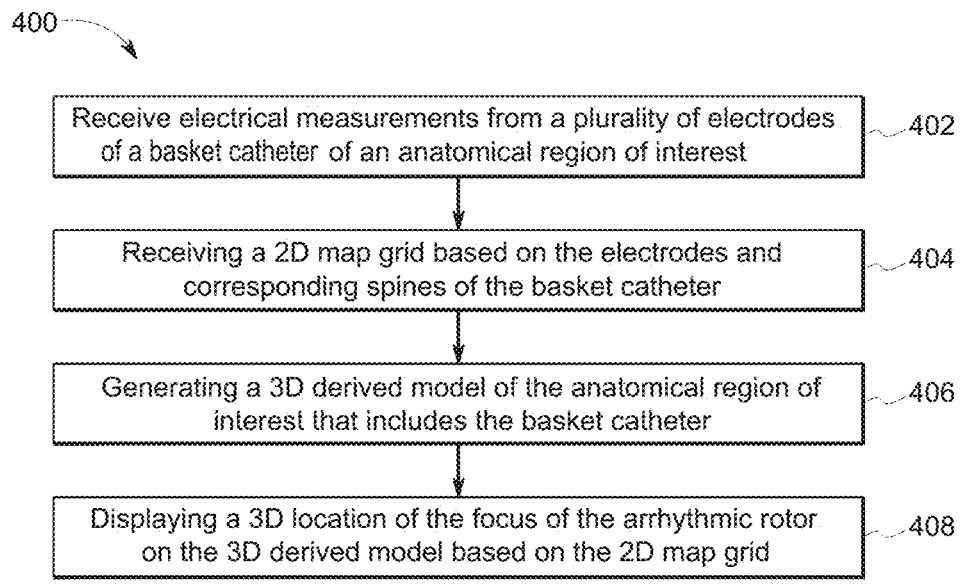
FIG. 4 is flowchart of a method for translating two dimensional mapping into a three dimensional derived model, in accordance with an embodiment.

FIG. 4 illustrates a flowchart of a method 400 for translating two dimensional (2D) mapping into a three dimensional (3D) derived model. The method 400, for example, may employ structures or aspects of various embodiments (e.g., systems and/or methods) discussed herein (e.g., the system 120 in FIG. 1, the basket catheter 200 in FIG. 2). In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. Furthermore, it is noted that the following is just one possible method of a magnetic tracker for surgical navigation. It should be noted, other methods may be used, in accordance with embodiments herein.

One or more methods may (i) receive electrical measurements from a plurality of electrodes of the basket catheter during at least one cardiac cycle of the heart, (ii) receive a 2D map grid based on the electrodes and corresponding spines of the basket catheter, (iii) generate a 3D derived model of the anatomical region of interest that includes the basket catheter, and (iv) display a 3D location of the focus of the arrhythmic rotor on the registered 3D model based on the 2D map grid.

Beginning at 402 the method 400 receives electrical measurements from a plurality of electrodes 222-236 of the basket catheter 132 of an anatomical region of interest. Optionally, the electrical measurements may be received during one or mode cardiac cycles of the heart measured by the basket catheter 132 or a heart monitoring system (e.g., electrocardiogram).

At 404, the 2D map grid 300 is received that is based on electrodes 222-236 and corresponding spines 206-216 of the basket catheter 132. The 2D map grid may include the location of at least one focus 380 of an arrhythmic rotor.

At 406, a 3D derived model 604 is generated of the anatomical region of interest (e.g., a chamber of a heart 504) that includes the basket catheter 502. The image processing subsystem 138 may receive image data from the EP recorder 134, the X-ray acquisition subsystem 162, the memory device 140, or the like. The image processing subsystem 138 may be configured to generate the 3D derived model 604 of the anatomical region and the current position or location of the basket catheter 502. The image processing subsystem 138, by generating the 3D derived model 604, allows identification of the spines 508 relative to the anatomical region of interest 504, and the electrodes (e.g., the electrodes 222-236) which are sequential down each spine 508.

Figure 5:
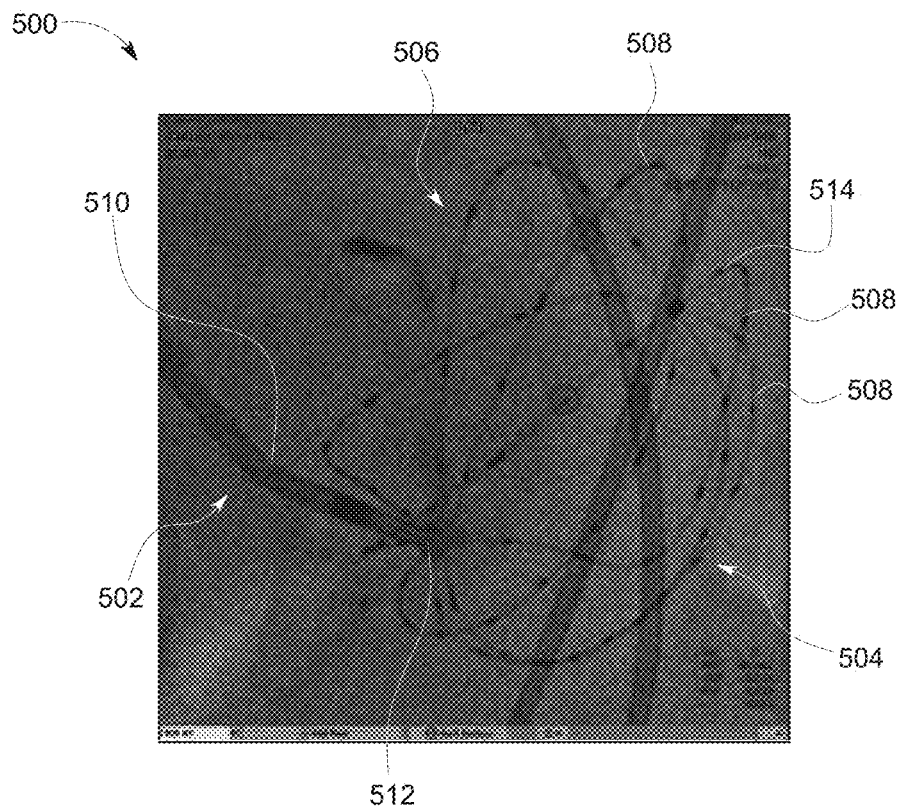
FIG. 5 illustrates a two dimensional image of an anatomical region of interest, in accordance with an embodiment.

For example, the image processing subsystem 138 may generate the 3D derived model 604 based on a 2D image of the anatomical region of interest that includes the basket catheter 502 and a 3D model 602 of the anatomical region of interest. FIG. 5 illustrates a 2D image 500 acquired from the X-ray acquisition subsystem 162 (e.g., fluoroscopy imaging system). For example, the clinician may position the basket catheter 502 into the anatomical region, such as a chamber of a heart 504. Once in position, the clinician may deploy the basket catheter 502 (e.g., deploy the basket catheter 502 into an expanded state) and instruct the X-ray acquisition subsystem 162 to acquire the 2D image 500 via the input device 144. Once the instruction is received by the clinician, the X-ray acquisition subsystem 162 may initiate a start sequence to the X-ray source 180 to generate X-rays into the anatomical region, which will be detected or received by the X-ray detector 181. The X-ray detector 181 generates data based on the detected X-rays and transfer the date to the X-ray acquisition subsystem 162. Based on the received data, the X-ray acquisition subsystem 162 generates the 2D image 500 and may output the 2D image 500 to the image processing subsystem 138. Optionally, X-ray acquisition subsystem 162 or the image processing subsystem 138 may output the 2D image 500 to the display device 142.

Figure 6:
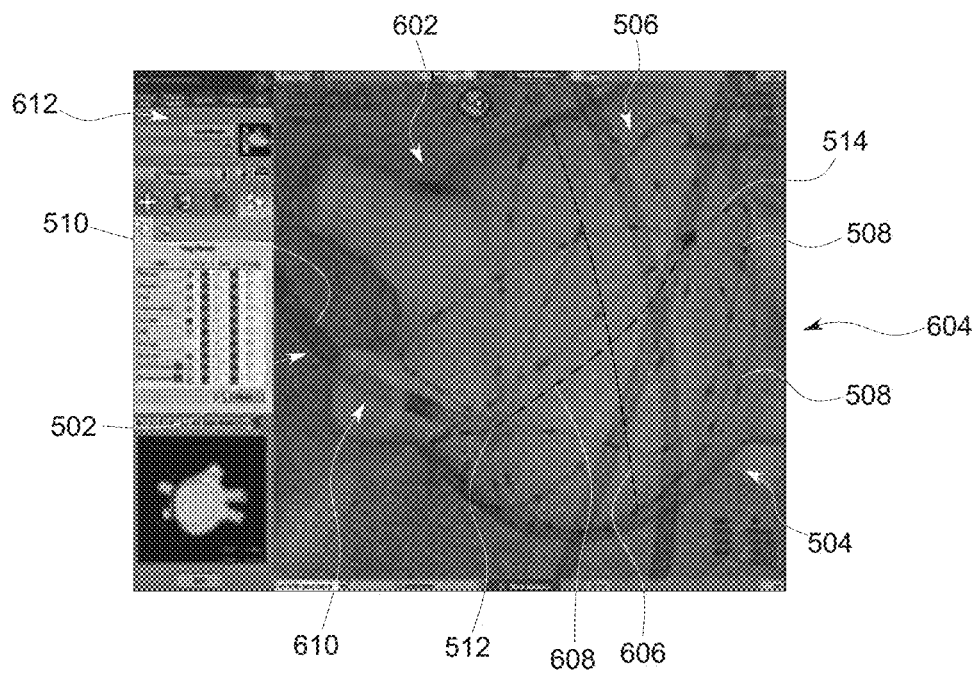
FIG. 6 illustrates a three dimensional derived model, in accordance with an embodiment.

FIG. 6 illustrates the 3D derived model 604 generated by the image processing subsystem 138 based on the 3D model 602 of the anatomical region and the 2D image 500 of the anatomical region 504. The image processing subsystem 138 may operably communicate or be communicatively coupled with the X-ray acquisition subsystem 162, EP recorder 134, the display device 142, the catheter input module 130, the memory device 410, the 2D mapping subsystem 136, the basket catheter 132, and the input device 144. Optionally, the image processing subsystem 138 is configured to induce the display device 142 to display a graphical user interface 612 allowing the user to view 2D images 500, 3D models 602, 3D derived models 604 or the like. The image processing subsystem 138 is further configured to store data, such as 2D images 500, 3D models 602, 3D derived models 604, or the like in the memory device 140.

The 3D derived model 604 may be generated by combining information from the 2D image 500 and the 3D model 602 of the anatomical region 504. As described above, the 3D model 602 may be based on an anatomical template stored on the image acquisition subsystem 162 and/or the memory device 140. Regarding the 2D image 500, the shape of an electrode assembly 506 of the basket catheter 502, being in the expanded state, conforms to the inner surface area of the anatomical region 504 (e.g., chamber of a heart) as the spines 508 are constrained by the anatomical region 504. The image processing subsystem 138 may generate the 3D derived model 604 by registering the 2D image 500 with the 3D model. Registration is the process of aligning, translating, and scaling the 3D model 602 to best fit the 2D image 500, specifically the basket catheter 502, to generate the 3D derived model 604.

Translation may include a number of parameters or degrees of freedom. For example, the basket catheter 502 of the 2D image 500 may behave as a rigid body, as the position has not changed significantly or was recently acquired. The registration subsystem 138 may include three translations and three rotations, which give six degrees of freedom, which may be used to adjust the position, rotation, or the like of the 3D model 602 relative to the basket catheter 502. Optionally, a set of corresponding mechanical features of the basket catheter 502 may be used as anatomical landmarks for the translation of the 3D model 602. For example, the translation of the 3D model 602 may be based on translating an aperture 610 of the anatomical region 504 to align with a position of the sheath 510 of the body catheter 502. Optionally, the clinician may change or adjust the translation of the 3D model 602 via the input device 144 or the graphical user interface 612 shown on the display device 142.

Scaling may include three degrees of freedom corresponding to each direction. The image processing subsystem 138 may be calibrated to approximate the size of the basket catheter 502 or the anatomical region 504 of the patient 166. Optionally, a set of corresponding mechanical features of the basket catheter 502 may be used as anatomical landmarks to adjust the size of the 3D model 602 such as a distal end 514 or proximal end 512 of the basket catheter. Additionally or alternatively, the image processing subsystem 138 may receive the size, dimensions, or the like of the 3D model 602 based on diameters 606 and 608 of the electrode assembly 506. For example, the position monitoring circuit 136 may determine the diameters 606 and 608 based on the position of the spines 508 within the anatomical region 504 of the patient 166 based on position electrodes. Optionally, the clinician may change or adjust the scaling or size of the 3D model 602 via the input device 144 or the graphical user interface 612 shown on the display device 142.

Figure 7:
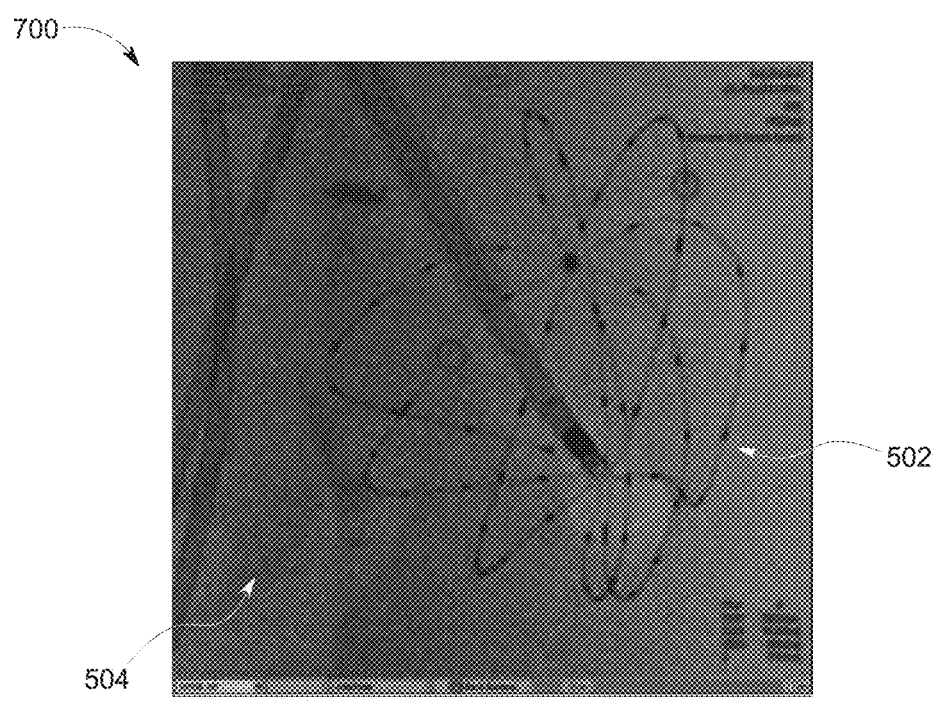
FIG. 7 illustrates a two dimensional image of an anatomical region of interest, in accordance with an embodiment.
Figure 8:
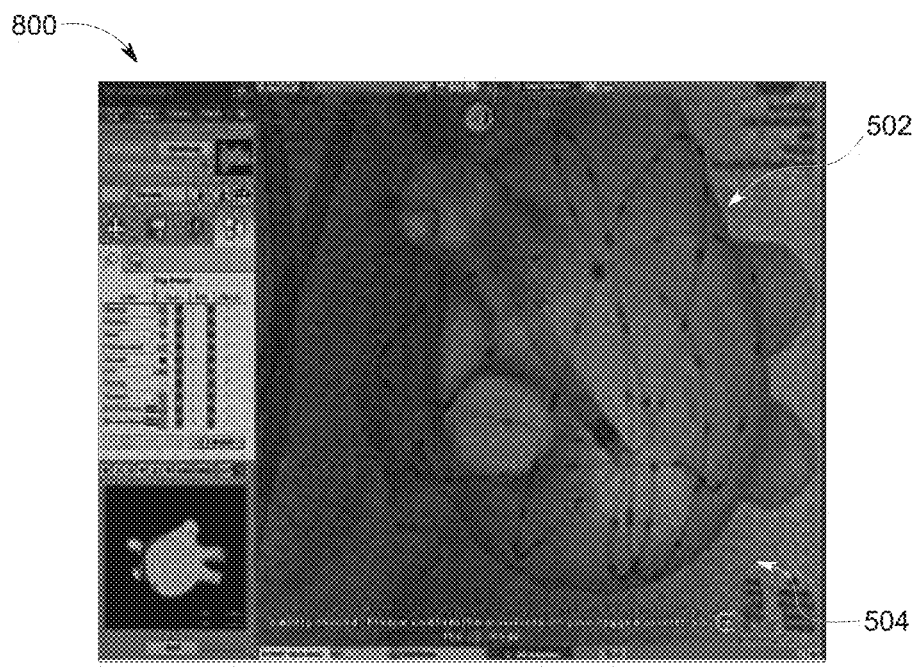
FIG. 8 illustrates a three dimensional derived model, in accordance with an embodiment.

Optionally, the image processing subsystem 138 may generate multiple 3D derived models based on a plurality of 2D images 500 generated by the X-ray acquisition subsystem 162. FIG. 7 illustrates an additional 2D image 702 acquired by the X-ray acquisition subsystem 162 of the basket catheter 502 within the anatomical region 504. The 2D image 702 may have been acquired at a different angle of the c-arm structure than that acquired for the 2D image 500. Based on the 2D images 500 and 700 and the 3D model 602, the image processing subsystem 138 may generate an additional 3D derived model 800, as described above.

Figure 9:
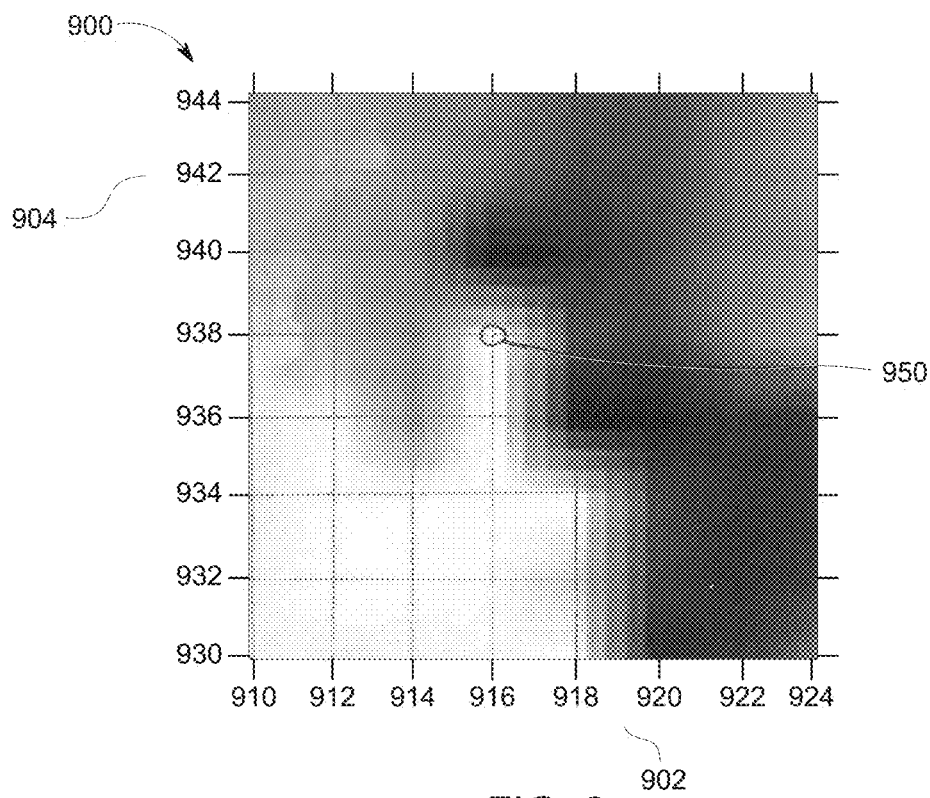
FIG. 9 is a two dimensional map grid of the electrical measurements of a basket catheter, in accordance with an embodiment.

At 408, a 3D location of a focus 950 of an arrhythmic rotor is displayed on the 3D derived model 1000 based on a 2D map grid 900. For example, the 2D mapping subsystem 136 may determine a location of a focus 950 of an arrhythmic rotor with respect to a basket catheter 1006 based on the electrical measurements, and the 2D map grid 900. FIG. 9 illustrates the 2D map grid 900 generated by the 2D mapping system 136 of the electrical measurements of the basket catheter 1006. The horizontal axis 902 is divided into spines 910-924 of the basket catheter 1006. The vertical axis 904 represents an electrode group 930-944 of the spines 910-924 based on a position of the electrode relative to the distal end 1008 of the sheath 1012. For example, the electrode group 930 may represent the electrodes proximate to the distal end 1008, and the electrode group 944 may represent the electrodes proximate to the distal end 1010 of the basket catheter 1006. The focus 950 is located or measured proximate to the spine 916 and the electrode group 938, or the fifth electrode from the distal end 1008.

Figure 10:
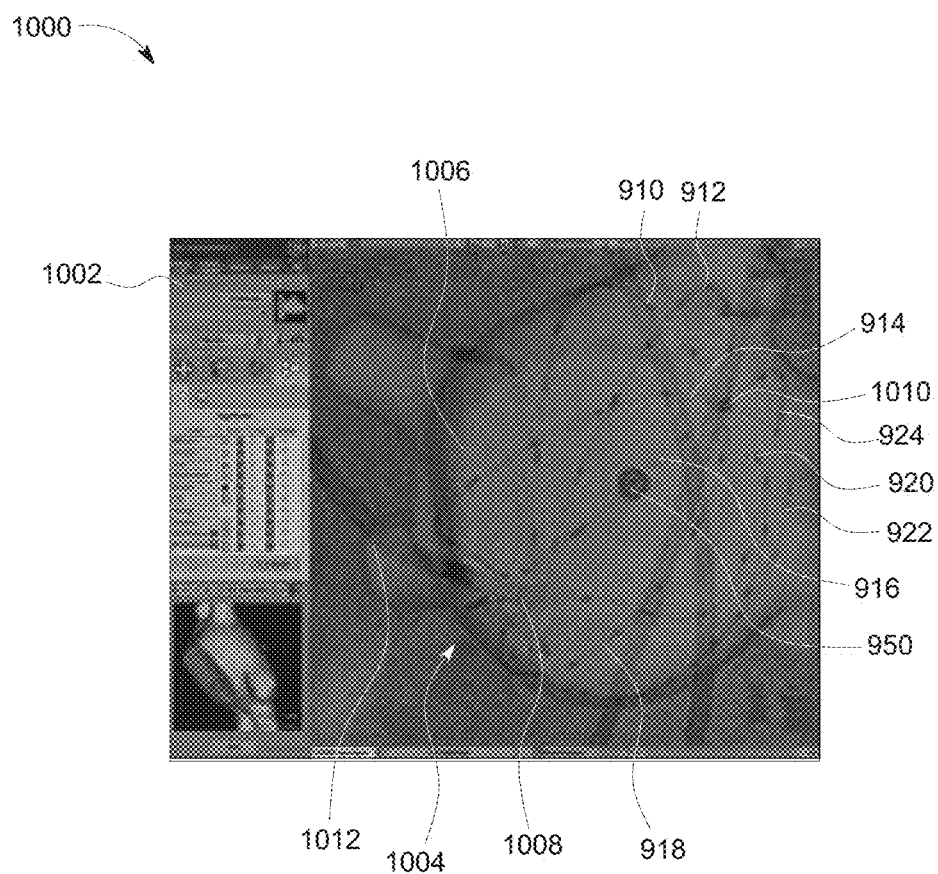
FIG. 10 illustrates a three dimensional derived model, in accordance with an embodiment.

FIG. 10 illustrates the 3D derived model 1000 generated by the image processing subsystem 138. The 3D derived model includes the basket catheter 1006. Based on the location of the focus 950 from the 2D map grid 900, the image processing subsystem 138 may overlay a marker 1014 over the focus 950 or the electrode proximate to the focus 950 determined from the 2D map grid 900.

Optionally, the registration subsystem 138 may receive the location of the focus 950 of an arrhythmic rotor on the 3D derived model 1000 from the input device 144. For example, the clinician may review the 3D derived model 1000 on the display device 142 and select the focus 950 using the input device 144 and/or using a graphical interface 1002 displayed on the display device 142. Optionally, the clinician may select the characteristics of the marker 1014, location of the focus 950, or the like using a graphical interface 1002 displayed on the display device 142. Additionally or alternatively, the image processing subsystem 138 may display the registered 3D model 1000 and the 2D map grid 900 concurrently.

Optionally, the method 400 may include determining a volume of the anatomical region based on a 3D model 1112, and selecting a basket catheter (e.g., the basket catheter 132) based on the volume. For example, the 3D model 1112 may be acquired of an anatomical region of interest from the X-ray acquisition system 162 (e.g., CT imaging system, a magnetic resonance (MR) imaging system, a 3D rotation angiography). The image processing subsystem 138 may receive an outline of the anatomical region from the input device 144 or a selection algorithm stored on the memory device 140 to determine the volume. Once the 3D model 1112 is acquired, the image processing subsystem 138 may calculate a volume of the anatomical region based on the 3D model 1112.

The image processing subsystem 138 may determine a basket catheter for the anatomical region of interest based on the volume. For example, the memory device 140 may include specification details of a plurality of basket catheters, such as, internal volume of electrode assembly in an expanded state. The image processing subsystem 138 may select one of the basket catheters 1102 for the anatomical region that has an internal volume of the electrode assembly in the expanded state within a predetermined threshold.

Figure 11:
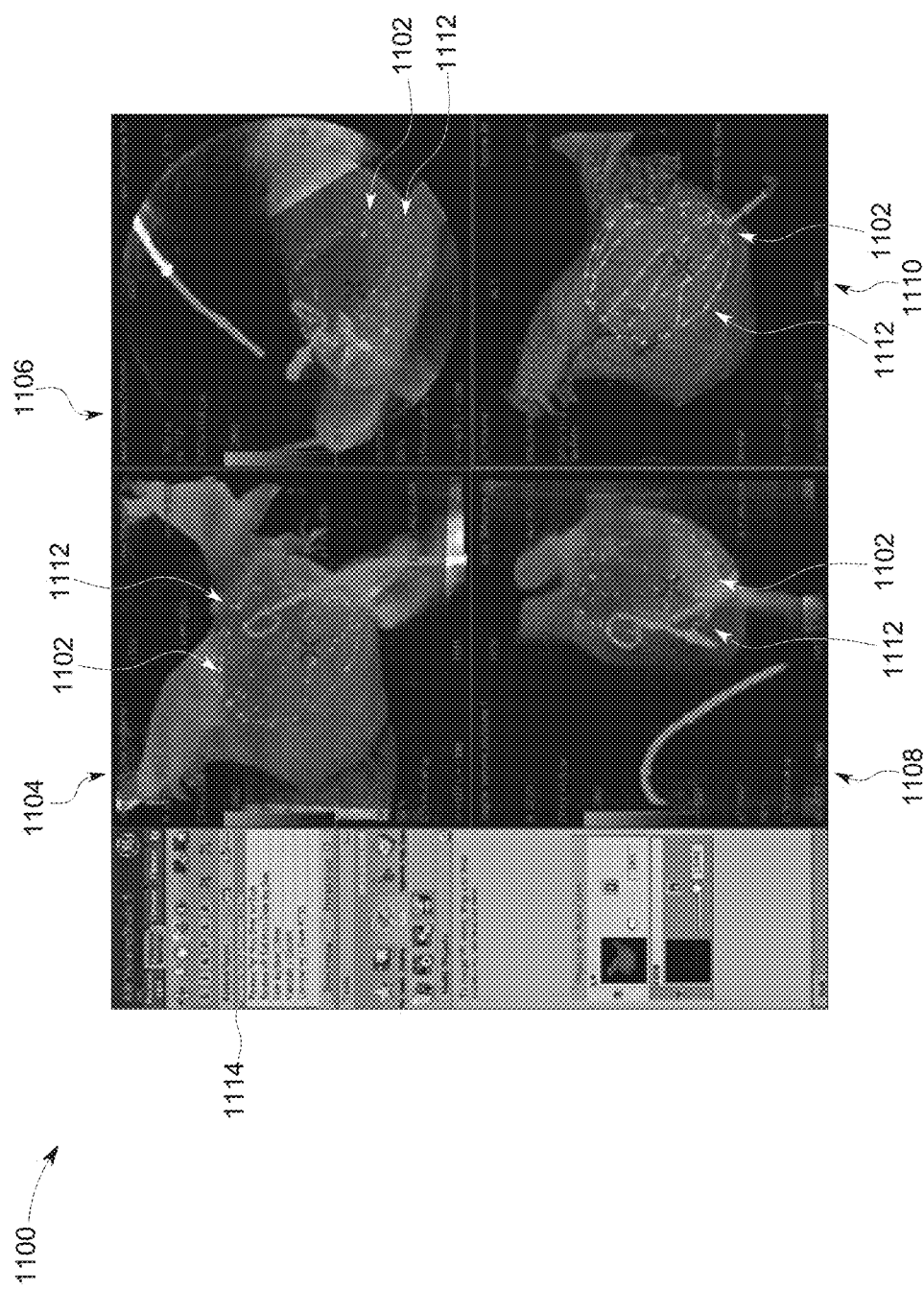
FIG. 11 illustrates three dimensional models of an anatomical region and a basket catheter, in accordance with an embodiment

Optionally, the image processing subsystem 138 may overlay the selected basket catheter 1102 over the 3D model 1110 on the display device 142. FIG. 11 illustrates four different angle views 1104-1110 of the 3D model 1112 that is displayed on the display device 142. It should be noted, that in embodiments fewer or more angle views may be generated on the display device 142. Additionally or alternatively, the image processing subsystem 138 may receive the selected basket catheter 1102 from the input device 144 and/or a graphical user interface 1114 displayed on the display device 142.

Optionally, the method 400 may include displaying a location marker on the 3D derived model representing a feature of the basket catheter 132. For example, the image processing subsystem 138 may overlay a location marker on the 3D derived model representing the distal 220, the proximal end 218, the sheath 202 or the like of the basket catheter 132.

It should be noted that the particular arrangement of components (e.g., the number, types, placement, or the like) of the illustrated embodiments may be modified in various alternate embodiments. For example, in various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), one or more aspects of one or more modules may be shared between modules, a given module or unit may be added, or a given module or unit may be omitted.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A method for translating two dimensional (2D) mapping of electrical measurements into a three dimensional (3D) derived model of an anatomical region, the method comprising:
    receiving electrical measurements from a plurality of electrodes of a basket catheter of an anatomical region of interest;
    receiving a 2D map grid based on the electrodes and corresponding spines of the basket catheter, wherein the 2D map grid includes a location of at least one focus of an arrhythmic rotor;
    generating a 3D derived model of the anatomical region of interest that includes the basket catheter; and
        displaying a 3D location of the focus of the arrhythmic rotor on the 3D derived model based on the 2D map grid.

2. The method of claim 1, further comprising acquiring a 2D image of the anatomical region of interest that include the basket catheter; and
    acquiring a 3D model of the anatomical region of interest, wherein the 3D derived model is based on the 2D image and the 3D model.

3. The method of claim 2, further comprising acquiring the 3D model from at least one of a CT imaging system, an MR imaging system, or a 3D rotational angiography;
    determining a volume of the anatomical region of interest based on the 3D model; and
    selecting the basket catheter from a plurality of basket catheters based on the volume of the anatomical region of interest.

4. The method of claim 2, further comprising acquiring the 2D image from a fluoroscopy imaging system.

5. The method of claim 2, further comprising acquiring a second 2D image, wherein the 3D derived model is further based on the second 2D image.

6. The method of claim 1, further comprising displaying the 2D map grid; and
    receiving from a user interface 3D location selections representing the focus of the arrhythmic rotor on the 3D derived model.

7. The method of claim 6, wherein the user interface includes a graphical user interface displayed on a display device.

8. The method of claim 1, wherein the 3D derived model is based on a priori information, the generating operation further comprises translating and scaling a 3D model of the anatomical region of interest.

9. The method of 1, further comprising displaying a location marker on the 3D derived model representing a feature of the basket catheter, wherein the feature is at least one of a distal or proximal end of the basket catheter.

10. The method of claim 1, further comprising receiving from a user interface 3D location selections that represent the focus of the arrhythmic rotor location.

11. A system for translating two dimensional (2D) mapping of electrical measurements into a three dimensional (3D) derived model of an anatomical region comprising:
    a basket catheter;
    a 2D mapping subsystem communicatively coupled to the basket catheter and an image processing subsystem, wherein the 2D mapping subsystem is configured to generate a 2D map grid based on electrical measurements from a plurality of electrodes received from the basket catheter, the 2D map grid includes a location of at least one focus of an arrhythmic rotor;
    the image processing subsystem is configured to generate a 3D derived model of an anatomical region of interest that includes the basket catheter; and
    a display device configured to display a 3D location of the focus of the arrhythmic rotor on the 3D derived model based on the 2D map grid.

12. The system of claim 11, wherein the basket catheter has an internal volume formed by the electrodes while in an expanded state, and the image processing subsystem is further configured to calculate a volume of the anatomical region of interest based on a 3D model, wherein the internal volume formed by the electrodes is within a predetermined threshold of the calculated volume of the anatomical region of interest.

13. The system of claim 11, wherein the image processing subsystem is configured to receive position measurements of the plurality of electrodes.

14. The system of claim 11, wherein the 3D derived model is based on a 3D model received by the image processing subsystem at least one of a group comprising a CT imaging system, an MR imaging system, or a 3D rotational angiography.

15. The system of claim 11, further comprising an input device, wherein the image processing subsystem is configured to receive from the input device 3D location selections representing the focus of the arrhythmic rotor on the 3D derived model.

16. The system of claim 11, wherein the 3D derived model is based on a 2D image received by the image processing subsystem from a fluoroscopy imaging system.

17. The system of claim 16, wherein the 3D derived model is further based on a second 2D image.

18. The system of claim 11, wherein the 3D derived model is based on a 3D model, the image processing subsystem is further configured to translating and scaling the 3D model to generate the 3D derived model.

19. The system of 11, wherein the display device is configured to display a 3D location marker on the 3D image representing a feature of the basket catheter, wherein the feature is at least one of a distal or proximal end of the basket catheter.

20. The system of claim 11, further comprising an input device, wherein the image processing subsystem receives from the input device location selections that represent the focus of the arrhythmic rotor location for the 3D derived model.

* * * * *